United States Patent
Addiego et al.

(10) Patent No.: US 11,554,232 B2
(45) Date of Patent: Jan. 17, 2023

(54) SWIVEL CONNECTOR ENDOTRACHEAL TUBE FOR SURGERY ON LOWER FACE AND NECK

(71) Applicants: Francesca Addiego, Media, PA (US); Christopher Hove, Paoli, PA (US)

(72) Inventors: Francesca Addiego, Media, PA (US); Christopher Hove, Paoli, PA (US)

( * ) Notice: Subject to any disclaimer, the term of this patent is extended or adjusted under 35 U.S.C. 154(b) by 662 days.

(21) Appl. No.: 16/577,856

(22) Filed: Sep. 20, 2019

(65) Prior Publication Data

US 2020/0114104 A1 Apr. 16, 2020

Related U.S. Application Data

(60) Provisional application No. 62/746,502, filed on Oct. 16, 2018.

(51) Int. Cl.
*A61M 16/00* (2006.01)
*A61M 16/04* (2006.01)
*A61M 16/08* (2006.01)

(52) U.S. Cl.
CPC .... *A61M 16/0463* (2013.01); *A61M 16/0402* (2014.02); *A61M 16/0833* (2014.02); *A61M 16/0875* (2013.01)

(58) Field of Classification Search
CPC .......... A61M 16/0463; A61M 16/0402; A61M 16/0833; A61M 16/0875
See application file for complete search history.

(56) References Cited

U.S. PATENT DOCUMENTS

| | | | | |
|---|---|---|---|---|
| 4,166,467 A * | 9/1979 | Abramson | ........ | A61M 16/0493 128/207.14 |
| 4,852,563 A * | 8/1989 | Gross | ................ | A61M 16/0833 285/305 |
| 5,062,420 A * | 11/1991 | Levine | .............. | A61M 16/0816 128/207.14 |
| 5,333,608 A * | 8/1994 | Cummins | ......... | A61M 16/0484 128/207.14 |
| 5,694,922 A * | 12/1997 | Palmer | .................. | A61M 39/26 128/207.14 |
| 5,735,271 A * | 4/1998 | Lorenzen | .......... | A61M 16/0833 128/207.14 |
| 11,298,487 B2 * | 4/2022 | McMurray | ........ | A61M 16/0402 |

* cited by examiner

*Primary Examiner* — Steven O Douglas
(74) *Attorney, Agent, or Firm* — Ryuh Patent Law; Steven Yu

(57) ABSTRACT

An endotracheal tube that is particularly useful for surgical operations on a patient's lower face. The endotracheal tube comprises a swivel segment and a laryngeal segment that are rotatably joined. To facilitate relocation of the endotracheal tube during surgery, the swivel segment can be swiveled in relation to the laryngeal segment. To allow instruments to be inserted, the swivel segment has a lumen access port that opens into the lumen of the swivel segment. The laryngeal segment may have a reinforced portion to prevent occlusion or damage by the patient biting. Also disclosed are methods for performing surgery on a patient's face using the endotracheal tube and methods of intubating a patient's airway using the endotracheal tube.

20 Claims, 4 Drawing Sheets

SWIVEL CONNECTOR ENDOTRACHEAL TUBE FOR SURGERY ON LOWER FACE AND NECK

TECHNICAL FIELD

This invention relates to endotracheal tubes, which are used to ventilate a patient's airway.

BACKGROUND

Endotracheal tubes are commonly used during surgical operations to secure and ventilate the patient. An endotracheal tube is typically a length of flexible tubing with a connector at its proximal end for attachment to a ventilator. Typically, for orotracheal intubation, the endotracheal tube is inserted through the patient's mouth and advanced along the patient's airway until the distal end of the endotracheal tube passes through the patient's larynx and into the trachea.

However, during surgery on the lower face, the endotracheal tube may present an obstruction to the surgical field. Examples of surgical situations where this may be a problem include extensive head/neck oncologic procedures, facial/mandibular/neck trauma surgery, maxillofacial surgery, or elective cosmetic surgery. In such situations, access to the nose, lower face, and neck are frequently necessary.

Having adequate surgical access to different areas of the face may require shifting, turning, or moving the endotracheal tube. But moving the endotracheal tube carries the risk of inadvertent extubation or endobronchial migration. Thus, there is a need for an endotracheal tube that allows improved surgical access to the lower face by facilitating free repositioning or relocation of the endotracheal tube, especially during surgery on the lower face.

Other patents for endotracheal tubes include the following:

| U.S. Patent/Publication No. | Inventor(s) | Issue/Pub. Date | Title |
| --- | --- | --- | --- |
| 6,378,523 | Christopher | Apr. 30, 2002 | Endotracheal tube having a beveled tip and orientation indicator |
| 4,852,564 | Sheridan | Aug. 1, 1989 | Flexible connectors for medico-surgical tubes |
| 5,245,992 | Nye | Sep. 21, 1993 | Tracheal tube with flexible segment |
| 2009/0211572 | Matera | Aug. 27, 2009 | Endotracheal intubation apparatus providing enhanced stability in an intubated patient |
| 4,050,466 | Koerbacher | Sep. 27, 1977 | Endotracheal tube |
| 9,364,628 | Hwang | Jun. 14, 2016 | Curvature-adjustable endotracheal tube |
| 5,333,608 | Cummins | Aug. 2, 1994 | Endotracheal tube for face, chin and neck surgery |

SUMMARY

This invention provides an endotracheal tube for insertion into a patient's trachea. As used herein, the terms "proximal" and "distal" are designated with respect to the direction of insertion into the patient's airway. The term "distal" in relation to the endotracheal tube means towards the insertion end (that end of the tube which is inserted into a patient), and the term "proximal" means towards the end that outwardly extends from the patient.

The endotracheal tube comprises a swivel segment and a laryngeal segment that are rotatably joined. The swivel segment is a tube structure having an elbow bend and at its proximal end, a connector for connecting to ventilation equipment. The laryngeal segment is a tube structure having an opening at its distal end. The lumen of the laryngeal segment is continuous with the lumen of the swivel segment. At its proximal end, the laryngeal segment is axially rotatably joined to the distal end of the swivel segment. In some embodiments, the laryngeal segment is rotatably joined to the swivel segment with sufficient resistance that the swivel segment is not loosely rotatable.

The elbow bend is located on a distal one-third section of the swivel segment. As used herein, the term "one-third section" is used in the context of an imaginary division of the swivel segment (or the laryngeal segment) into three sections of equal length: a proximal one-third section, a middle one-third section, and a distal one-third section.

The laryngeal segment may have any suitable length. In some embodiments, the length of the laryngeal segment is 27 cm or shorter; in some cases, 25 cm or shorter. The length of the laryngeal segment is at least 5 cm. In some embodiments, the length of the laryngeal segment is in the range of 19-27 cm; and in some cases, in the range of 21-25 cm.

In some embodiments, the length of the swivel segment is 11 cm or shorter; in some cases, 9 cm or shorter. The length of the swivel segment is at least 3 cm. In some embodiments, the length of the swivel segment is in the range of 3-11 cm; in some cases, in the range of 5-9 cm.

The swivel segment has a lumen access port that opens into the lumen of the swivel segment. In some embodiments, the lumen access port is located on a distal one-third section of the swivel segment. In some embodiments, the endotracheal tube further comprises a gas-tight removable cap for the lumen access port; in some cases, the endotracheal tube further comprises a tether that is attached to the cap. In some embodiments, there is no such lumen access port on the laryngeal segment.

In some embodiments, the laryngeal segment further comprises a reinforced portion at a proximal one-third section of the laryngeal segment. Reinforced construction of the laryngeal segment at the reinforced portion can be provided in any suitable way, such as wire-reinforcement of the wall, using a double wall, hardened materials, etc. Reinforced construction could also be provided by making the tube wall thicker at the reinforced portion. In some embodiments, the reinforced portion of the laryngeal segment has a tube wall that is thicker than the tube wall at a portion of the laryngeal segment that is distal to the reinforced portion. In some embodiments, the tube wall at the reinforced portion is at least 3 mm thick; and in some cases, at least 5 mm thick. The tube wall at the reinforced portion may be up to 10 mm thick. In some cases, the thickness of the tube wall at the reinforced portion is in the range of 3-7 mm thick.

The laryngeal segment may have any of various features that are found in conventional endotracheal tubes. For example, the endotracheal tube of the invention may have radiopaque feature(s), such as a radiopaque stripe or radiopaque markers. The laryngeal segment may have visual indicators, such as vocal cord markers or depth/length markings in centimeters.

In another aspect, this invention is a method of intubating a patient's airway. The method comprises inserting an endotracheal tube of the invention, via the oral or nasal route, into the patient's trachea. A variety of different types of clinicians (e.g. physician, nurse, respiratory therapist, paramedic, etc.) may be able to perform this method. The method further comprises connecting the connector of the swivel segment to ventilation equipment. In some embodiments, the method further comprises positioning the reinforced portion at the patient's teeth and securing the endotracheal tube in this position.

In some embodiments, the method further comprises inserting an instrument (such as a suction catheter, flexible endoscope, or intubation stylet) into the lumen access port of the endotracheal tube. The instrument is advanced through the laryngeal segment of the endotracheal tube. In the case of a suction catheter, suctioning of the patient's airway is performed using the suction catheter. In some embodiments, the instrument is inserted through the lumen access port in a direction parallel to the longitudinal axis of the laryngeal segment; and in some cases, coaxial to the longitudinal axis of the laryngeal segment. In some embodiments, the instrument is inserted through the lumen access port in a downward direction (relative to the ground) towards the lumen of the laryngeal segment.

In some embodiments, the step of inserting the instrument does not require uncoupling the endotracheal tube from the ventilation equipment. In some embodiments, the step of inserting the instrument is performed while the endotracheal tube is still coupled to the ventilation equipment. In some embodiments, the step of inserting the instrument excludes the step of uncoupling the endotracheal tube from the ventilation equipment.

This endotracheal tube may be particularly useful when performing surgery on a patient's lower face. Accordingly, in another aspect, this invention is a method of performing surgery on a patient's lower face (i.e. at the level of the nose and below), such as the areas of the nose, mouth, or chin (e.g. maxillofacial surgery). The method comprises intubating, orally or nasally, the patient with an endotracheal tube of the invention. The method further comprises: performing surgery on a first part of the patient's lower face; swiveling the swivel segment away from a second part of the patient's lower face, wherein the second part is different from the first part; and performing surgery on the second part of the patient's lower face.

DETAILED DESCRIPTION

Figure 1:
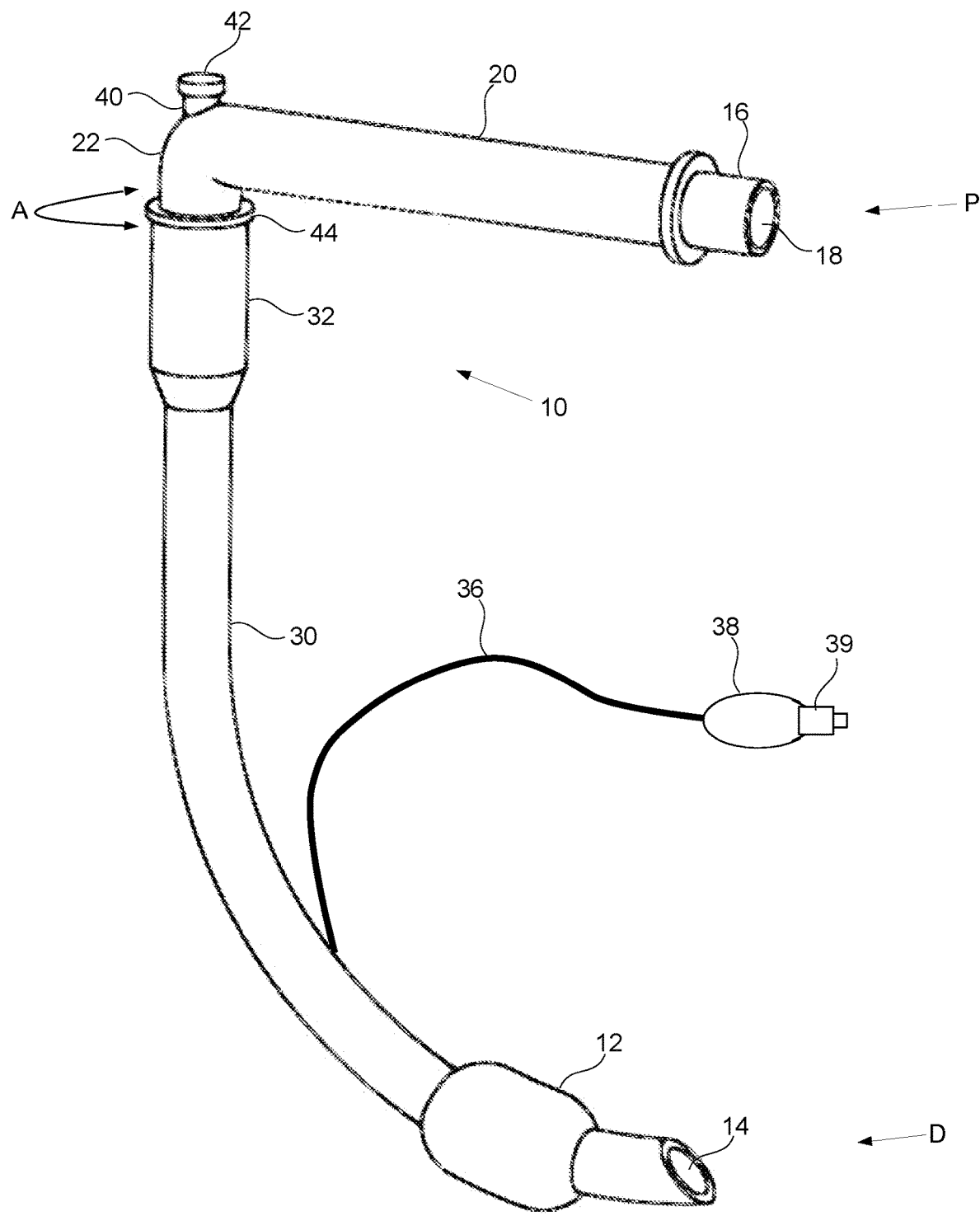
FIG. 1 shows a perspective view of an example endotracheal tube of the invention.
Figure 2A:
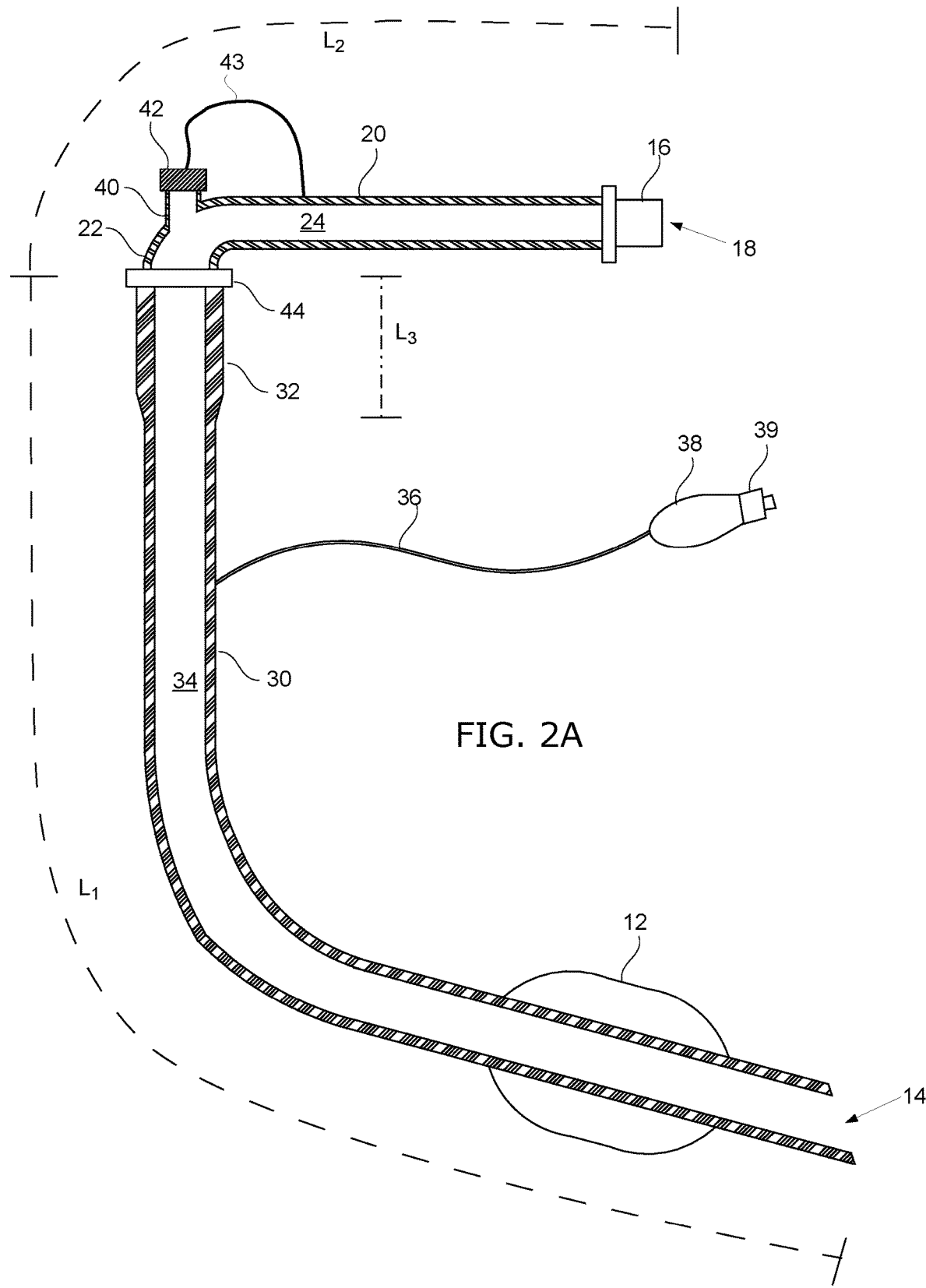
FIG. 2A shows a cross-section view of the endotracheal tube shown in FIG. 1.
Figure 2B:
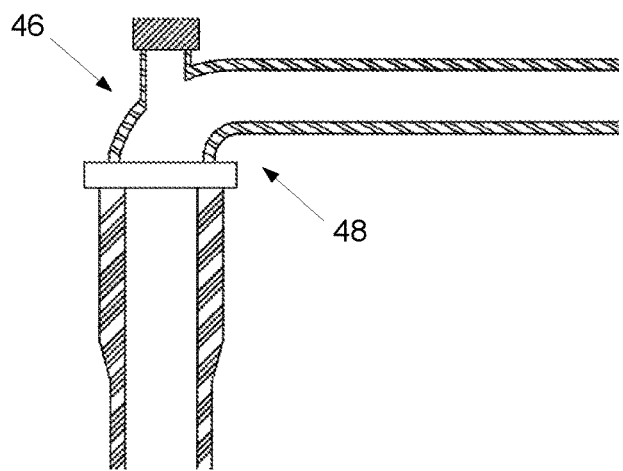
FIG. 2B shows a close-up view of the elbow bend on the endotracheal tube.

To assist in understanding the invention, reference is made to the accompanying drawings to shown by way of illustration specific embodiments in which the invention may be practiced. FIGS. 1, 2A, and 2B show an example endotracheal tube 10 of the invention. FIG. 1 shows a perspective side view; FIG. 2A shows a cross-section side view; FIG. 2B shows a close-up of the cross-section view. The arrow labeled "P" indicates the proximal end and "D" indicate the distal end. The endotracheal tube 10 comprises two tube segments, the laryngeal segment 30 and the swivel segment 20, that are joined to each other.

1. Laryngeal Segment. The laryngeal segment 30 is the part of the endotracheal tube 10 that is inserted into the patient's airway. The laryngeal segment 30 is a tube structure with a lumen 34. At the distal end of the laryngeal segment 30, the endotracheal tube 10 has an opening 14 at the beveled tip for ventilation of the trachea through the endotracheal tube 10.

At the proximal end of the laryngeal segment 30, the tube wall has a thicker, reinforced portion 32. During intubation, this reinforced portion 32 is positioned at the incisor teeth of the patient's mouth. This reinforced portion 32 protects the endotracheal tube 10 from occlusion or damage by the patient biting. As such, the reinforced portion 32 is sufficiently thick and hard to protect the endotracheal tube 10 from biting by the patient. In some embodiments, the reinforced portion 32 extends from the proximal end of the laryngeal segment 30 to a distance of at least 4 cm distal from the proximal end of the laryngeal segment 30 (shown as length $L_3$ in FIG. 2A).

In addition to making the endotracheal tube more crush-resistant against the patient's teeth and jaws, having this reinforced portion 32 may provide a number of other benefits. For example, in many conventional situations, an oral airway is placed into the patient's mouth as a "bite block" as a precaution to secure airway access at the end of a case when the patient is emerging from anesthesia. However, such oral airways often cause undesirable coughing. Moreover, such oral airways can be easily pushed out by the tongue. As such, this reinforced portion 32 may serve as a safer substitute for an oral airway.

It may be beneficial for the reinforced portion 32 to be sufficiently wide to give enough space between the upper and lower teeth to allow oral suctioning via a Yankauer-type suction tip. This could be a safety feature that allows use of a large suction tip for suctioning out any gastric content debris that has flowed into the mouth. As such, in some embodiments, the outer diameter of the reinforced portion 32 is at least at least 12 mm; in some cases, at least 15 mm; in some cases, at least 18 mm; in some cases, at least 22 mm.

Near the distal end of the laryngeal segment 30, there is an inflatable cuff 12 that is attached to the exterior surface of the laryngeal segment 30. Inflation of the cuff 12 is controlled through a small inflation line 36 by connecting a syringe to the syringe connector 39. The inflated cuff 12 forms a seal against the tracheal wall to allow positive pressure ventilation without air leakage, as well as serving as a barrier against mucus and secretions. A pilot balloon 38 inflates when the cuff 12 meets resistance from the trachea to indicate sufficient inflation of the cuff 12.

The laryngeal segment 30 is sufficiently long that, with the reinforced portion 32 positioned at the incisor teeth, its distal opening 14 and inflatable cuff 12 are positioned in the trachea. The length of the laryngeal segment 30 is designated by length $L_1$ in FIG. 2A. Some suitable lengths for $L_1$ are given above.

The laryngeal segment 30 has a curvature to help conform to the shape of the airway. The laryngeal segment 30 should be sufficiently flexible to follow the contour of the patient's airway without requiring excessive force and to accommodate variations in patient size and anatomy. However, the laryngeal segment 30 must have sufficient rigidity to be advanced into the patient's airway without buckling. As such, this laryngeal segment 30 may have a stiffness similar to that of a conventional endotracheal tube.

2. Swivel Segment. The swivel segment 20 is the part of the endotracheal tube 10 that provides a connection to the ventilation equipment. The swivel segment 20 is a tubular structure with a lumen 24, which is continuous with the lumen 34 of the laryngeal segment 30. At its proximal end, the swivel segment 20 is joined to a standard 15 mm connector 16 (not shown in cross-section in FIG. 2A for better clarity) for connection, directly or indirectly, to any suitable type of ventilation equipment, such as a mechanical ventilator, a valved air bag, or the like. Connector 16 has a proximal opening 18. The length of swivel segment 20 is designated by $L_2$ in FIG. 2A. Some suitable lengths for $L_2$ are given above.

3. Swivel Connection. At its proximal end, the laryngeal segment 30 is joined to the distal end of the swivel segment 20 by a swivel joint 44 (not shown in cross-section in FIG. 2A for better clarity), which allows the swivel segment 20 to be axially rotatable relative to the laryngeal segment 30. That is, the swivel segment 20 can be rotated relative to the laryngeal segment 30 about the longitudinal axis of the laryngeal segment 30. Any suitable gas-tight mechanism can be used to rotatably join the laryngeal segment 30 to the swivel segment 20. Such mechanisms could include various types of seals, sliding mechanisms, slots, ridges, edges, flanges, sleeves, ball bearings or bearing-like surface, or other types of swivel fittings or adapters.

The joining mechanism and the endotracheal tube 10 are constructed in a manner such that swivel segment 20 and laryngeal segment 30 are not detachable from each other (under ordinary manual pulling force). This feature is important because, otherwise, accidental separation of the two segments could result in the laryngeal segment 30 becoming dislodged into the oropharynx. The joining mechanism is designed such that swivel segment 20 does not freely swivel under ordinary handling or gravity. There is sufficient resistance that it will only swivel with gentle, but intentional manual force being applied. This feature may be useful for preventing the swivel segment 20 from swinging uncontrollably during the act of intubation, which can be an annoyance for the operator and interfere with swift intubation. To allow for swiveling relative to the laryngeal segment 30, near its distal end, the swivel segment 20 has an elbow bend 22. The angle of the elbow bend 22 allows the two segments to be easily swiveled. In some embodiments, the angle between the longitudinal axis of the laryngeal segment 30 and the main longitudinal axis of the swivel segment 20 is in the range of 70-110°; and in some cases, in the range of 80-100°; and in some cases, about 90°. The swivel segment 20 with its elbow bend 22 is constructed as a single unitary, rigid structure made of polyethylene.

4. Lumen Access Port. At the elbow bend 22, there is a lumen access port 40 located on the swivel segment 20. The swivel segment 20 being non-detachable from the laryngeal segment 30, this lumen access port 40 provides a safe and convenient access to the lumen of the endotracheal tube 10 without having to uncouple the connection to the ventilation equipment. This lumen access port 40 represents a significant safety feature not present in existing endotracheal tube designs. FIG. 2B shows a close-up view of the elbow section 22. This view shows a clearer view of the outer curvature 46 and inner curvature 48 of the elbow bend. As seen here, the lumen access port 40 is located on the outer curvature of the elbow bend 22.

A gas-tight removable cap 42 covers the opening to the lumen access port 40 when not in use. The removable cap 42 is designed with a Luer-lock fitting for secure attachment. To avoid inadvertent loss when uncapped (e.g. accidentally dropping it), the removable cap 42 is tethered to swivel segment 20 via a short (2-3 cm length) flexible tether 43 (shown in FIG. 2A). Alternatively, the tether 43 could be attached to a collar looped around the neck of the lumen access port 40.

The lumen access port 40 is sized such that a suction catheter can be inserted through the lumen access port 40. In some embodiments, the inner diameter of the lumen access port 40 is less than 10 mm wide; in some cases, less than 7 mm wide. The lumen access port 40 could also be used for other functions, such as allowing insertion of other types of instruments such as intubating stylets or flexible endoscopes, administering medications or fluids, etc.

5. Other Features. As mentioned above, the laryngeal segment 30 has some degree of flexibility to follow the contour of the patient's airway without requiring excessive force and to accommodate variations in patient size and anatomy. But because the swivel segment 20 resides externally, no such flexibility is required for the swivel segment 20. As such, in some embodiments, the swivel segment 20 is more rigid than the laryngeal segment 30.

A radiopaque stripe (not shown) is incorporated along the length of the laryngeal segment 30. This radiopaque stripe can be imaged under x-ray to confirm placement of the endotracheal tube 10. The radiopaque stripe can also serve as a visual indicator for the clinician to indicate the rotational orientation of the distal tip of the endotracheal tube 10.

Figure 3A:
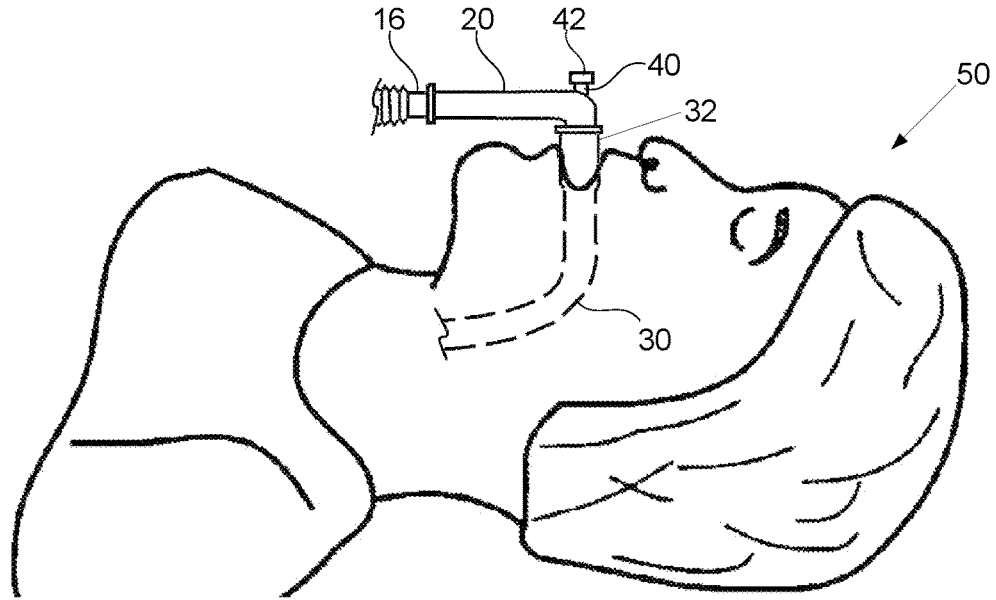
FIGS. 3A and 3B show an endotracheal tube inserted into a patient's airway.
Figure 3B:
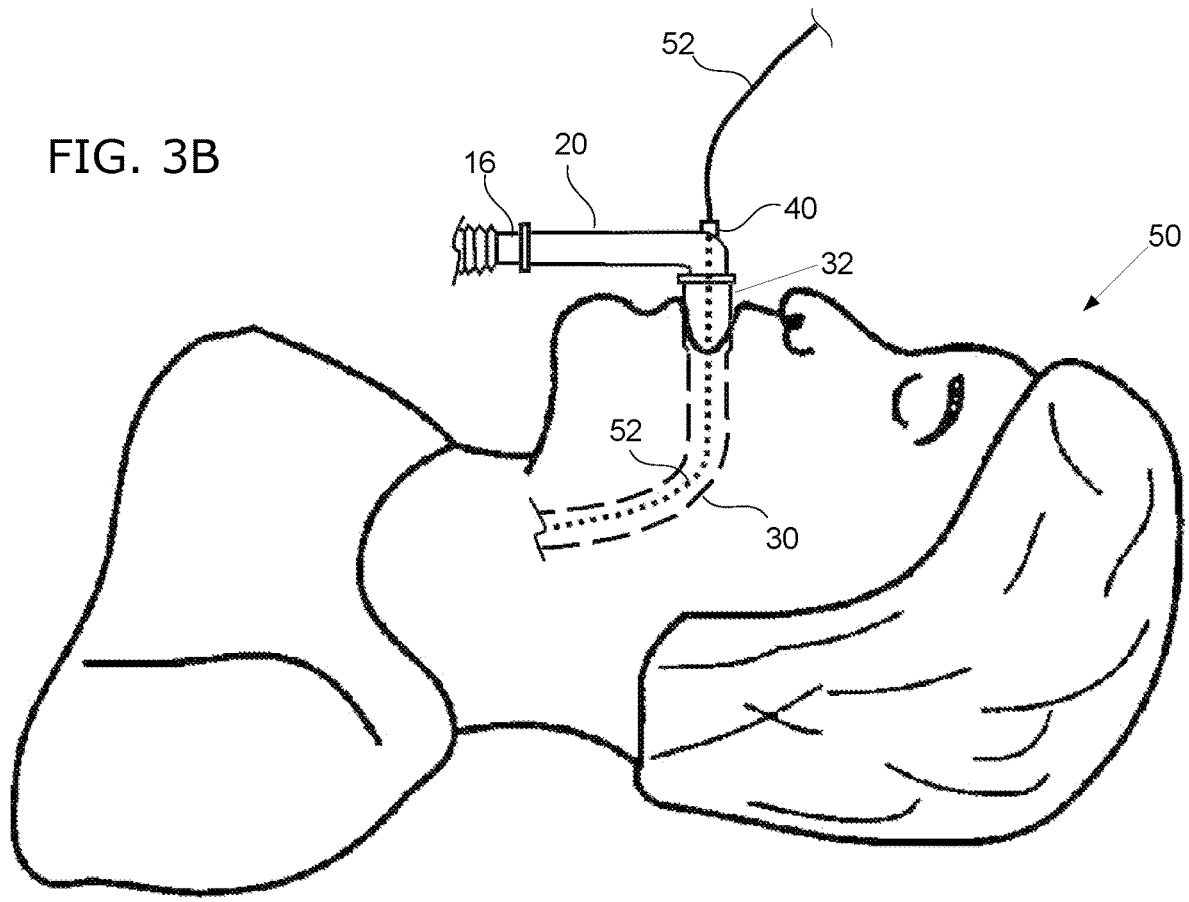

6. Method of Use. FIGS. 3A and 3B show an example of how the endotracheal tube 10 could be used in patient care. For inserting the endotracheal tube 10, the clinician takes a position at the head of the supine patient 50 above the patient's mouth. The clinician bends forward over the patient's head to look directly downward at the patient. The distal end of the endotracheal tube 10 is then inserted into the patient's mouth. If a conventional guide blade is used to facilitate insertion, the endotracheal tube 10 is typically inserted at a slight angle toward the top of the patient's head, so that the anterior side of the endotracheal tube 10 faces upward to some degree.

The endotracheal tube 10 is then advanced past the epiglottis and into the patient's airway. At the patient's larynx, the distal tip of the endotracheal tube 10 is made to pass through the opening between the vocal cords. After this insertion of the endotracheal tube 10, the cuff 12 at the distal end of the endotracheal tube 10 is inflated via the inflation line to seal the patient's airway surrounding the endotracheal tube 10. The endotracheal tube 10 is then connected to a mechanical ventilator via its standard 15 mm connector 16 at the proximal end of the endotracheal tube 10. Alternatively, the endotracheal tube 10 could be inserted via the nasopharyngeal airway.

FIG. 3A shows the endotracheal tube 10 positioned in the patient's airway. Note that the reinforced portion 32 of the laryngeal segment 30 is positioned at the patient's incisor teeth. As seen in this view, this helps to protect the endotracheal tube 10 when the patient bites down. FIG. 3B shows how routine airway suctioning could be performed with the endotracheal tube 10 in place. The cap 42 to the lumen access port 40 is removed to allow access to the lumen of the endotracheal tube 10. A suction catheter 52, which is connected to a suction unit, is inserted downward into the lumen access port 40, into the lumen of the swivel segment 20, and through the laryngeal segment 30. The suction catheter 52 is then advanced out of the distal opening 14 of the laryngeal segment 30 and into the patient's trachea for suctioning out of secretions, mucous, debris, etc. The reinforced portion 32 of the laryngeal segment 30 separates the patient's teeth with a gap wide enough to permit oral suctioning by a large Yankauer-type suction tip. Using a large suction tip may be particularly useful if the patient's gastric content debris has flowed into the mouth.

Figure 4:
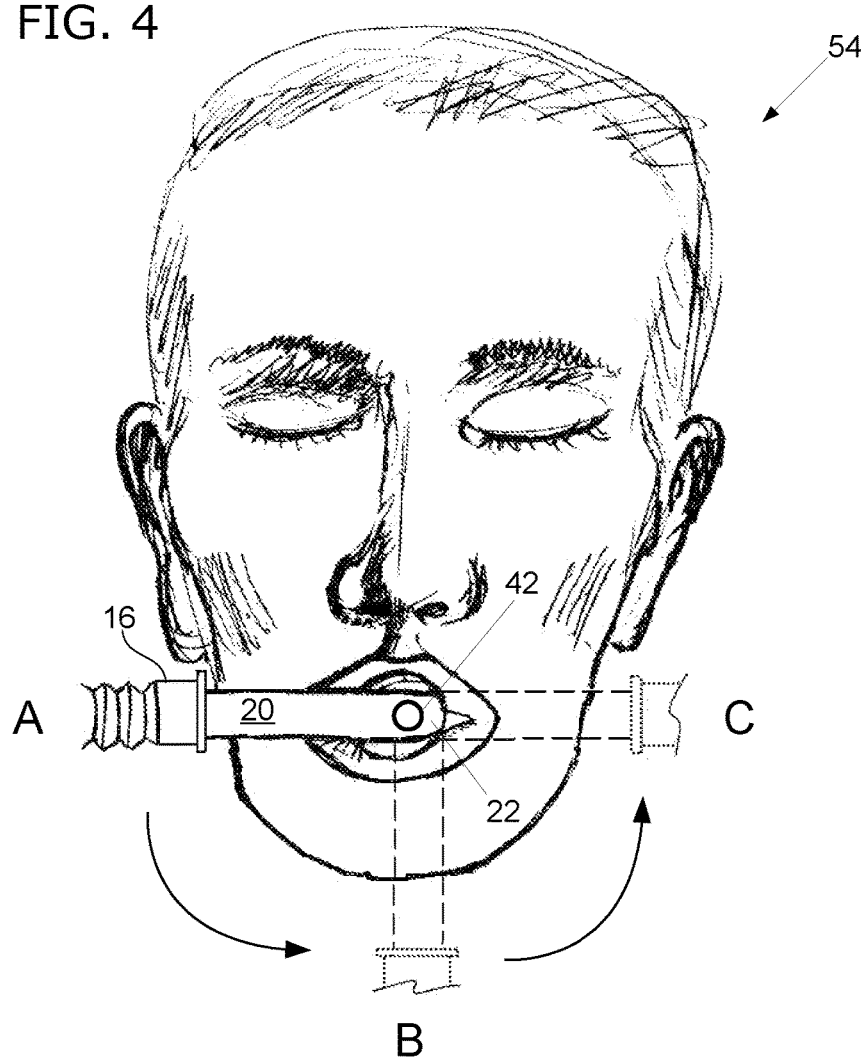
FIG. 4 shows an endotracheal tube being swiveled to various positions around the patient's lower face.

FIG. 4 shows an example of how the endotracheal tube 10 could be easily swiveled to various positions to facilitate relocation of the endotracheal tube during facial surgery. Positioning of the endotracheal tube 10 in orientation A gives surgical access to the left side of the patient's 54 lower face and chin areas, allowing the surgical procedure to focus on those areas of the patient's face. Next, the endotracheal tube 10 is swiveled to orientation B (caudal direction) to improve access to the nasal area of the patient's face, allowing the surgical procedure to focus on this area of the patient's face. Next, the endotracheal tube 10 is swiveled to orientation C to improve access to the right side of the patient's face, allowing the surgical procedure to focus on this area of the patient's face.

The foregoing description and examples have been set forth merely to illustrate the invention and are not intended to be limiting. Each of the disclosed aspects and embodiments of the invention may be considered individually or in combination with other aspects, embodiments, and variations of the invention. In addition, unless otherwise specified, the steps of the methods of the invention are not confined to any particular order of performance. Modifications of the disclosed embodiments incorporating the spirit and substance of the invention may occur to persons skilled in the art, and such modifications are within the scope of the invention.

Any use of the word "or" herein is intended to be inclusive and is equivalent to the expression "and/or," unless the context clearly dictates otherwise. As such, for example, the expression "A or B" means A, or B, or both A and B. Similarly, for example, the expression "A, B, or C" means A, or B, or C, or any combination thereof.

The invention claimed is:

1. An endotracheal tube for insertion into a patient's trachea, the endotracheal tube comprising:
   a swivel segment being a tube with a lumen, the swivel segment having an elbow bend and at its proximal end, a connector for connecting to ventilation equipment; and wherein the swivel segment does not freely swivel under gravity;
   a laryngeal segment being a tube with a lumen, the laryngeal segment having an opening at its distal end, and at its proximal end, is axially rotatably and non-detachably joined to the distal end of the swivel segment such that the lumen of the laryngeal segment is continuous with the lumen of the swivel segment;
   a lumen access port on the swivel segment and opening into the lumen of swivel segment.
2. The endotracheal tube of claim 1, wherein the lumen access port is located on an outer curvature of the elbow bend.
3. The endotracheal tube of claim 1, wherein the elbow bend is located at a distal one-third section of the swivel segment.
4. The endotracheal tube of claim 3, wherein the lumen access port is located at the distal one-third section of the swivel segment.
5. The endotracheal tube of claim 1, further comprising a removable cap for the lumen access port.
6. The endotracheal tube of claim 1, wherein the laryngeal segment further comprises a reinforced portion at a proximal one-third section of the laryngeal segment.
7. The endotracheal tube of claim 6, wherein the reinforced portion is a tube wall that is thicker than the tube wall at a portion of the laryngeal segment that is distal to the reinforced portion.
8. The endotracheal tube of claim 7, wherein the thickness of the tube wall at the reinforced portion is at least 3 mm.
9. The endotracheal tube of claim 1, wherein the laryngeal segment has a length of 27 cm or shorter.
10. The endotracheal tube of claim 1, wherein the swivel segment has a length of 11 cm or shorter.
11. The endotracheal tube of claim 1, further comprising at the proximal end of the swivel segment, a standard 15 mm connector for connecting to ventilation equipment.
12. A method of intubating a patient's airway, comprising:
    having an endotracheal tube of claim 1;
    inserting the endotracheal tube into the patient's trachea via an oral route;
    connecting the connector of the swivel segment to ventilation equipment;
    inserting a suction catheter into the lumen access port of the endotracheal tube;
    advancing the suction catheter through the laryngeal segment and out the distal opening;
    using the suction catheter, suctioning the patient's airway.
13. The method of claim 12, wherein the endotracheal tube further comprises a cap on the lumen access port, and the method comprises removing the cap on the lumen access port.
14. The method of claim 12, wherein the laryngeal segment further comprises a reinforced portion at a proximal one-third section of the laryngeal segment, and wherein the method further comprises positioning the reinforced wall at the patient's incisor teeth and securing the endotracheal tube in this position.
15. The method of claim 12, wherein the suction catheter is inserted through the lumen access port in a direction parallel to the longitudinal axis of the laryngeal segment.
16. The method of claim 12, wherein the step of inserting a suction catheter is performed while the endotracheal tube is still coupled to the ventilation equipment.
17. The method of claim 12, wherein the lumen access port is located on an outer curvature of the elbow bend.
18. The method of claim 12, wherein the endotracheal tube further comprises at the proximal end of the flexible tubular portion, a standard 15 mm connector for connecting to ventilation equipment; and
    wherein the method further comprises connecting the endotracheal tube to the ventilation equipment via the standard 15 mm connector.
19. A method of performing surgery on a patient's lower face, comprising:
    inserting an endotracheal tube of claim 1, into the patient's airway via an oral route;
    performing surgery on a first part of the patient's lower face;
    swiveling the swivel segment to an orientation away from a second part of the patient's lower face, wherein the second part is different from the first part;
    performing surgery on the second part of the patient's lower face.
20. The method of claim 19, wherein the laryngeal segment further comprises a reinforced portion at a proximal one-third section of the laryngeal segment, and wherein the method further comprises positioning the reinforced wall at the patient's incisor teeth and securing the endotracheal tube in this position.

* * * * *